United States Patent [19]

Miller

[11] Patent Number: 5,045,471
[45] Date of Patent: Sep. 3, 1991

[54] CLONED DNA FOR P450SCC AND EXPRESSION THEREOF

[75] Inventor: Walter L. Miller, San Francisco, Calif.

[73] Assignee: The Regents of the University of California, Oakland, Calif.

[21] Appl. No.: 936,883

[22] Filed: Dec. 2, 1986

[51] Int. Cl.$^5$ ............... C12N 15/52; C12N 15/70; C12N 15/74; C12N 15/79

[52] U.S. Cl. .................. 435/320.1; 435/641; 435/70.1; 435/71.1; 435/91; 435/172.1; 435/172.3; 435/240.1; 435/252.3; 536/27

[58] Field of Search ............. 435/6, 68, 70, 69.1, 435/70.1, 71.1, 172.1, 91, 172.3, 240.1, 252.3, 320; 935/13, 4, 9, 6, 22, 59, 66; 536/27

[56] References Cited

U.S. PATENT DOCUMENTS 4,720,454  1/1988  White et al. .................... 435/6
4,757,020  7/1988  Beppu et al. ................... 435/253

OTHER PUBLICATIONS

Matteson, K. J., et al., Study of Cholesterol Side-Chain Cleavage (20, 22 Demolase), Deficiency Cogentital Lipoid Adrenal Hyperplasia Using Bovine-Sequence P450scc Oligodeoxyribonucleotide Probes, *Endocrinology* (1986), 118 (4): 1296.

Morohashi, K., et al., Molecular Cloning and Nucleotide Sequence of cDNA for mRNA of Mitochrondrial Cytochrome P-450(scc) of Bovine Adrenal Cortex, *Proc. Natl. Acad. Sci. USA* (1984), 81: 4651.

*Primary Examiner*—Richard A. Schwartz
*Assistant Examiner*—Richard C. Peet
*Attorney, Agent, or Firm*—Richard L. Neeley

[57] ABSTRACT

A polynucleotide sequence encoding human P450scc is disclosed along with techniques for utilizing the P450scc expressed by this gene to reduce in vivo cholesterol levels.

9 Claims, 3 Drawing Sheets

GGGCGCTGAAGTGGAGCAGGTACAGTCACAGCTGTGGGGACAGC

```
1                                                    10
Met Leu Ala Lys Gly Leu Pro Pro Arg Ser Val Leu Lys Gly
ATG CTG GCC AAG GGT CTT CCC CCA CGC TCA GTC CTG GTC AAA GGC 20                                              30
Tyr Gln Thr Phe Leu Ser Ala Pro Arg Glu Gly Leu Gly Arg Leu
TAC CAG ACC TTT CTG AGT GCC CCC AGG GAG GGG CTG GGG CGT CTC

40
Arg Val Pro Thr Gly Glu Gly Ala Gly Ile Ser Thr Arg Ser Pro
AGG GTG CCC ACT GGC GAG GGA GCT GGC ATC TCC ACC CGC AGT CCT 50                                      60
Arg Pro Phe Asn Glu Ile Pro Ser Pro Gly Asp Asn Gly Trp Leu
CGC CCC TTC AAT GAG ATC CCC TCT CCT GGT GAC AAT GGC TGG CTA

70
Asn Leu Tyr His Phe Trp Arg Glu Thr Gly Thr His Lys Val His
AAC CTG TAC CAT TTC TGG AGG GAG ACG GGC ACA CAC AAA GTC CAC 80                                          90
Leu His His Val Gln Asn Phe Gln Lys Tyr Gly Pro Ile Tyr Arg
CTT CAC CAT GTC CAG AAT TTC CAG AAG TAT GGC CCG ATT TAC AGG

100
Glu Lys Leu Gly Asn Val Glu Ser Val Tyr Val Ile Asp Pro Glu
GAG AAG CTC GGC AAC GTG GAG TCG GTT TAT GTC ATC GAC CCT GAA 110                                         120
Asp Val Ala Leu Leu Phe Lys Ser Glu Gly Pro Asn Pro Glu Arg
GAT GTG GCC CTT CTC TTT AAG TCC GAG GGC CCC AAC CCA GAA CGA

130
Phe Leu Ile Pro Pro Trp Val Ala Tyr His Gln Tyr Tyr Gln Arg
TTC CTC ATC CCG CCC TGG GTC GCC TAT CAC CAG TAT TAC CAG AGA 140                                         150
Pro Ile Gly Val Leu Leu Lys Lys Ser Ala Ala Trp Lys Lys Asp
CCC ATA GGA GTC CTG TTG AAG AAG TCG GCA GCC TGG AAG AAA GAC

160
Arg Val Ala Leu Asn Gln Glu Val Met Ala Pro Glu Ala Thr Lys
CGG GTG GCC CTG AAC CAG GAG GTG ATG GCT CCA GAG GCC ACC AAG 170                                     180
Asn Phe Leu Pro Leu Leu Asp Ala Val Ser Arg Asp Phe Val Ser
AAC TTT TTG CCC CTG TTG GAT GCA GTG TCT CGG GAC TTC GTC AGT

190
Val Leu His Arg Arg Ile Lys Lys Ala Gly Ser Gly Asn Tyr Ser
GTC CTG CAC AGG CGC ATC AAG AAG GCG GGC TCC GGA AAT TAC TCG
```

FIGURE (Page 1 of 3)

```
                         200                                              210
      Gly Asp Ile Ser Asp Asp Leu Phe Arg Phe Ala Phe Glu Ser Ile
      GGG GAC ATC AGT GAT GAC CTG TTC CGC TTT GCC TTT GAG TCC ATC

220
      Thr Asn Val Ile Phe Gly Glu Arg Gln Gly Met Leu Glu Glu Val
      ACT AAC GTC ATT TTT GGG GAG CGC CAG GGG ATG CTG GAG GAA CTA 230                                              240
      Val Asn Pro Glu Ala Gln Arg Phe Ile Asp Ala Ile Tyr Gln Met
      CTG AAC CCC GAG GCC CAG CGA TTC ATT GAT GCC ATC TAC CAG ATG

250
      Phe His Thr Ser Val Pro Met Leu Asn Leu Pro Pro Asp Leu Phe
      TTC CAC ACC AGC GTC CCC ATG CTC AAC CTT CCC CCA GAC CTG TTC 260                                              270
      Arg Leu Phe Arg Thr Lys Thr Trp Lys Asp His Val Ala Ala Trp
      CGT CTG TTC AGG ACC AAG ACC TGG AAG GAC CAT GTG GCT GCA TGG

280
      Asp Val Ile Phe Ser Lys Ala Asp Ile Tyr Thr Gln Asn Phe Tyr
      GAC GTG ATT TTC AGT AAA GCT GAC ATA TAC ACC CAG AAC TTC TAC 290                                              300
      Trp Glu Leu Arg Gln Lys Gly Ser Val His His Asp Tyr Arg Gly
      TGG GAA TTG AGA CAG AAA GGA AGT GTT CAC CAC GAT TAC CGT GGC

310
      Met Leu Tyr Arg Leu Leu Gly Asp Ser Lys Met Ser Phe Glu Asp
      ATG CTC TAC AGA CTC CTG GGA GAC AGC AAG ATG TCC TTC GAG GAC 320                                              330
      Ile Lys Ala Asn Val Thr Glu Met Leu Ala Gly Gly Val Asp Thr
      ATC AAG GCC AAC GTC ACA GAG ATG CTG GCA GGA GGG GTG GAC ACG

340
      Thr Ser Met Thr Leu Gln Trp His Leu Tyr Glu Met Ala Arg Asn
      ACG TCC ATG ACC CTG CAG TGG CAC TTG TAT GAG ATG GCA CGC AAC 350                                              360
      Leu Lys Val Gln Asp Met Leu Arg Ala Glu Val Leu Ala Ala Arg
      CTG AAG GTG CAG GAT ATG CTG CGG GCA GAG GTC TTG GCT GCG CGG

370
      His Gln Ala Gln Gly Asp Met Ala Thr Met Leu Gln Leu Val Pro
      CAC CAG GCC CAG GGA GAC ATG GCC ACG ATG CTA CAG CTG GTC CCC 380                                              390
      Leu Leu Lys Ala Ser Ile Lys Glu Thr Leu Arg Leu His Pro Ile
      CTC CTC AAA GCC AGC ATC AAG GAG ACA CTA AGA CTT CAC CCC ATC

400
      Ser Val Thr Leu Gln Arg Tyr Leu Val Asn Asp Leu Val Leu Arg
      TCC GTG ACC CTG CAG AGA TAT CTT GTA AAT GAC TTG GTT CTT CGA
```

FIGURE (Page 2 of 3)

```
                    410                                          420
Asp Tyr Met Ile Pro Ala Lys Thr Leu Val Gln Val Ala Ile Tyr
GAT TAC ATG ATT CCT GCC AAG ACA CTG GTG CAA GTG GCC ATC TAT

430
Ala Leu Gly Arg Glu Pro Thr Phe Phe Phe Asp Pro Glu Asn Phe
GCT CTG GGC CGA GAG CCC ACC TTC TTC TTC GAC CCG GAA AAT TTT 440                                          450
Asp Pro Thr Arg Trp Leu Ser Lys Asp Lys Asn Ile Thr Tyr Phe
GAC CCA ACC CGA TGG CTG AGC AAA GAC AAG AAC ATC ACC TAC TTC

460
Arg Asn Leu Gly Phe Gly Trp Gly Val Arg Gln Cys Leu Gly Arg
CGG AAC TTG GGC TTT GGC TGG GGT GTG CGG CAG TGT CTG GGA CGG 470                                          480
Arg Ile Ala Glu Leu Glu Met Thr Ile Phe Leu Ile Asn Met Leu
CGG ATC GCT GAG CTA GAG ATG ACC ATC TTC CTC ATC AAT ATG CTG

490
Glu Asn Phe Arg Val Glu Ile Gln His Leu Ser Asp Val Gly Thr
GAG AAC TTC AGA GTT GAA ATC CAA CAC CTC AGC GAT GTG GGC ACC 500                                          510
Thr Phe Asn Leu Ile Leu Met Pro Glu Lys Pro Ile Ser Phe Thr
ACA TTC AAC CTC ATT CTG ATG CCT GAA AAG CCC ATC TCC TTC ACC 520 521
Phe Trp Pro Phe Asn Gln Glu Ala Thr Gln Gln OP
TTC TGG CCC TTT AAC CAG GAA GCA ACC CAG CAG TGA TCAGAGAGGAT

GGCCTGCAGCCACATGGGAGGAAGGCCCAGGGGTGGGGCCCATGGGGTCTCTGCATCTT

CAGTCGTCTGTCCCAAGTCCTGCTCCTTTCTGCCCAGCCTGCTCAGCAGGTTGAATGGG

TTCTCAGTGGTCACCTTCCTCAGCTCAGCTGGGCCACTCCTCTTCACCCACCCCATGGA

GACAATAAACAGCTGAACCATCGAAAAAAAAAAAAAAAAAA
```

FIGURE (Page 3 of 3)

CLONED DNA FOR P450SCC AND EXPRESSION THEREOF

This invention was made with Government support under Grant No. HD16047 awarded by the National Institutes of Health. The Government has certain rights in the invention.

FIELD OF THE INVENTION

This invention is most closely related to the fields of genetic engineering and enzymology and is particularly directed to polynucleotide constructs and their expression to produce enzymes and to the use of the enzymes so produced as reagents both in laboratory and pharmaceutical applications.

BACKGROUND OF THE INVENTION

Conversion of cholesterol to pregnenolone is the first and rate-limiting step in the synthesis of all steroid hormones. This conversion entails three steps: 20-hydroxylation, 22-hydroxylation, and cleavage of the $C_{20}$–$C_{22}$ bond to produce pregnenolone and isocaproic acid. These three steps are mediated by a single mitochondrial cytochrome, formerly known as 20,22-desmolase and now identified as P450scc. P450scc is the cholesterol-specific terminal oxidase in a mitochondrial electron transport system consisting of a flavoprotein (adrenodoxin reductase), an iron-sulfur protein (adrenodoxin), and cytochrome P450scc. Deficient P450scc activity causes lipoid adrenal hyperplasia, a generally lethal disease.

There are a number of related cytochrome P450 enzymes. Microsomal cytochrome P450's catalyze a wide variety of oxidation reactions of endogenous substrates as well as xenobiotics, including drugs. On the contrary, mitochondrial cytochrome P450's show no known enzyme activities to xenobiotics.

The molecular cloning and nucleotide sequence of cDNA for mitochondrial cytochrome P450scc of bovine adrenal cortex has been reported. However, the corresponding cDNA, mRNA, chromosomal DNA, and/or primary amino acid sequence of human mitochondrial cytochrome P450scc was not known prior to the present invention. Bovine mitochondrial cytochrome P450scc has not been utilized in humans, at least in part because of its unknown activity and potential antigenicity in humans as a result of its different primary amino acid sequence.

Accordingly, there is need for techniques of preparing human mitochondrial cytochrome P450scc (preferably by techniques of genetic engineering), and for developing its use in reducing cholesterol levels in humans.

BRIEF DESCRIPTION OF RELEVANT LITERATURE

The molecular cloning and nucleotide sequence of cDNA for mRNA of mitochondrial cytochrome P450scc of bovine adrenal cortex is described in Morohashi et al., *Proc. Natl. Acad. Sci. USA* (1984) 81:4647–4651. A previous publication from the inventor's own laboratory, Matteson et al., *Endochronology* (1986) 118:1296–1305, described a P450scc cDNA fragment containing nucleotides encoding the carboxy-terminal half of the human P450scc protein.

SUMMARY OF THE INVENTION

Polynucleotide molecules encoding the complete human P450scc protein are provided for use in polynucleotide constructs for synthesizing the cytochrome. Human P450scc itself is provided for use in the therapy of atherosclerosis and other disorders in which a reduction in cholesterol level is desired.

BRIEF DESCRIPTION OF THE DRAWINGS

The present invention will be better understood by reference to the following detailed description of specific embodiments when considered in connection with the drawings that form part of this specification, wherein:

The FIGURE shows the sequence of human P450scc cDNA and the corresponding amino acid sequence deduced from the genetic code. The codons and the amino acid positions are numbered beginning with the methionine initiation codon as 1.

DESCRIPTION OF SPECIFIC EMBODIMENTS

The present inventor has obtained for the first time recombinant DNA vectors capable of expressing the human protein P450scc in a microorganism and has additionally identified for the first time the amino acid sequence of human P450scc, thereby providing access to homogeneous human P450scc. Using this information a variety of recombinant DNA vectors capable of providing homogeneous P450scc in reasonable quantities are obtained. Additional recombinant DNA vectors can be produced using standard techniques of recombinant DNA technology.

The amino acid sequence of a typical molecule of P450scc is shown in the FIGURE, which also gives a complete polynucleotide sequence encoding the peptide. Since the DNA sequence encoding the peptide has been fully identified, it is possible to produce such a DNA sequence entirely by synthetic chemistry, after which the sequence can be inserted into any of the many available DNA vectors using known techniques of recombinant DNA technology. Thus the present invention can be carried out using reagents, plasmids, and microorganisms which are freely available and in the public domain at the time of filing of this patent application.

For example, nucleotide sequences greater than 100 bases long can be readily synthesized on an Applied Biosystems Model 380A DNA Synthesizer as evidenced by commercial advertising of the same (e.g., *Genetic Engineering News*, November/December 1984, p. 3). Such oligonucleotides can readily be spliced using, among others, the techniques described later in this application to produce any nucleotide sequence described herein.

Furthermore, automated equipment is also available that makes direct synthesis of any of the peptides disclosed herein readily available. In the same issue of *Genetic Engineering News* mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the biological activity of the resulting molecule, especially if the replacement does not involve an amino acid at a binding site. Whether a change results in a functioning peptide can readily be determined by incubating the resulting peptide in a solution containing cholesterol, a flavoprotein, and an iron-sulfur protein and monitoring the appearance of pregnenolone. Examples of this process are described later in detail. If pregnenolone is detected, the replacement is immaterial, and the molecule being tested is equivalent to that of the FIGURE, although the rate may vary from that of the specific peptide shown. Peptides in which more than one replacement has taken place can readily be tested in the same manner.

DNA molecules that code for such peptides can readily be determined from a list of equivalent codons and are likewise contemplated as being equivalent to the DNA sequence of the FIGURE. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

In addition to the specific nucleotides in the expressed portion of the sequence identified in the FIGURE, DNA (or corresponding RNA) molecules of the invention can have additional nucleotides preceeding or following the coding region other than those that are specifically listed. For example, poly A can be added to the 3'-terminal, short (e.g., fewer than 20 nucleotides) sequence can be added to either terminal to provide a terminal sequence corresponding to a restriction endonuclease site, stop codons can follow the peptide sequence to terminate transcription, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation of additional DNA from biological sources.

The DNA sequence encoding human P450scc is sometimes referred to in this specification as a gene, the term "gene" being used in the sense of a polynucleotide sequence encoding a peptide. The actual human gene is referred to as "human genomic DNA".

Peptides of the invention can be prepared for the first time as homogeneous preparations, either by direct synthesis or by using a cloned gene as described herein. By "homogeneous" is meant, when referring to a peptide or DNA sequence, that the primary molecular structure (i.e., the sequence of amino acids or nucleotides) of substantially all molecules present in the composition under consideration is identical. The term "substantially" as used herein preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogenity since the term "homogeneous" relates to the presence of entire molecules (and fragments thereof) have a single defined structure as opposed to mixtures in which several molecules of similar molecular weight are present but which differ in their primary molecular structure. The term "isolated" as used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acylamide gel) but not obtained either as pure substances or as solutions. The term "pure" as used herein preferably has the same numerical limits as "substantially" immediately above. The phrase "replaced by" or "replacement" as used herein does not necessarily refer to any action that must take place but to the peptide that exists when an indicated "replacement" amino acid is present in the same position as the amino acid indicated to be present in a different formula (e.g., when isoleucine is present at position 2 instead of leucine).

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

DNA segments coding for peptides of the invention can be prepared synthetically as described above or, utilizing labeled probes prepared from short, synthetically prepared oligonucleotides, mRNA and/or cDNA can be isolated from human cell lines. These techniques can be used to obtain not only fragments of specific nucleotide sequences related to a desired protein, but also the entire nucleotide sequence coding for the protein of interest. Double-stranded, chemically synthesized oligonucleotide linkers, containing the recognition sequence for a restriction endonuclease, may be attached to the ends of the isolated cDNA, to facilitate subsequent enzymatic removal of the gene portion from the vector DNA. See Scheller et al., *Science* (1977) 196:177. The vector DNA is converted from a continuous loop to a linear form by treatment with an appropriate restriction endonuclease. The ends thereby formed are treated with alkaline phosphatase to remove 5'-phosphate end groups so that the vector DNA may not reform a continuous loop in a DNA ligase reaction without first incorporating a segment of the P450scc DNA. The cDNA, with attached linker oligonucleotides, and the treated vector DNA are mixed together with a DNA ligase enzyme, to join the cDNA to the vector DNA, forming a continuous loop of recombinant vector DNA, having the cDNA incorporated therein. Where a plasmid vector is used, usually the closed loop will be the only form able to transform a bacterium. Transformation, as is understood in the art and used herein, is the term used to denote the process whereby a microorganism incorporates extracellular DNA into its own genetic constitution. Plasmid DNA in the form of a closed loop may be so incorporated under appropriate environmental conditions. The incorporated closed loop plasmid undergoes replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used. Once a recombinant vector has been made, transformation of a suitable microorganism is a straightforward process, and novel microorganism strains containing the human P450scc gene may readily be isolated, using appropriate selection techniques, as understood in the art.

Although the sequence of steps set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of P450scc can be enhanced by including multiple copies of the P450scc gene in a transformed host, by selecting a vector known to reproduce in the host, thereby producing large quantities of protein from exogeneous inserted DNA (such as pUC8, ptac12, or pIN-III-ompA1, 2, or 3), or by any other known means of enhancing peptide expression.

In all cases, P450scc will be expressed when the DNA sequence is functionally inserted into the vector. By "functionally inserted" is meant in proper reading frame and orientation, as is well understood by those skilled in the art. Typically, a P450scc gene will be inserted downstream from a promoter and will be followed by a stop codon, although production as a hybrid protein, optionally followed by cleavage, may be used if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that unlimited supplies of human P450scc will become available for use in development of pharmacological intervention in vivo in the reduction of cholesterol levels, particularly treatment of atherosclerosis. The protein will also be available for use (optionally in labeled form) as a standard in immunoassays and other assays intended to determine the presence of the normal enzyme in humans. Polypeptides of the invention can also be used in the preparation of monoclonal antibodies and antisera used in diagnostic techniques. Fragments of the total peptide, particularly fragments involving hydrophilic (i.e., polar, acidic, and basic amino acids) that are likely to be present on the outer surface of the peptide represent preferred fragments for use in generating antibodies. Preferred are regions of indefinite length having at least 50% hydrophilic residues, more preferably at least 75% hydrophilic residues. Especially preferred regions associated with enzyme activity are identified in the discussion of Table 1 in the following Example. Peptides of at least 5 amino acids up to the full length of these regions are preferred.

When peptides of the invention are utilized in the treatment of disorders in which a patient is being treated to reduce an in vivo cholesterol concentration, a functional P450scc protein is administered to the patient in an amount effective to reduce the desired concentration. The term concentration here is used in its broadest sense to include deposits of cholesterol that have formed on arterial walls and in other in vivo interior spaces. Reduction of elevated serum cholesterol levels is also a goal of the present invention.

When P450scc is administered by itself, its activity depends on the presence of endogenous amounts of the remainder of the electron transport system, namely adrenodoxin and adrenodoxin reductase. The invention may also be carried out by administering P450scc concurrently with an exogenous flavoprotein and exogenous iron-sulfur protein. Exogenous adrenodoxin and adrenodoxin reductase are preferred.

One useful way to administer combinations of these proteins is in the form of liposomes surrounding all three of the components. Those components that are normally associated with membranes become associated with the liposome membrane while the non-membrane components are retained within the interior of the liposome.

Administration can be by any means in which peptides are administered to the location in which a cholesterol concentration reduction is desired. Since reductions in blood concentrations are particularly important, intravenous injection is a preferred method of administration. However, other techniques that will result in introduction of an effective amount of human P450scc to the desired location can be utilized. Examples include intramuscular and subcutaneous injections. Because of enzymatic degradation in the stomach and small intestine, oral administration is less desirable although oral administration may be useful in case of high oral intake of cholesterol by acting to degrade cholesterol before it is absorbed and before the enzyme itself is degraded. Recent advances in preparing compositions containing proteins for oral ingestion, typically developed for oral administration of insulin, can be utilized for the oral administration of human P450scc.

The effective amount to be administered will vary from patient to patient depending on the amount of endogenous enzyme present and the degree to which cholesterol levels are high and in need of reduction. Accordingly, effective amounts are best determined by the physician administering the enzyme. However, a useful initial amount for administration is in the range of from 0.1 to 100 mg, preferably from 1 to 10 mg for a 70-kg adult. After allowing sufficient time for the enzyme to take effect (typically 24 hours), analysis of the current cholesterol level and comparison to the initial level prior to administration will determine whether the amount being administered is too low, within the right range, or too high. As an initial guideline, because of the intimate contact of blood with other cholesterol deposits within the body and the exchange of cholesterol between carrier proteins in the blood and various deposits of cholesterol, administration of human P450scc to provide a reduction of serum cholesterol to any extent is considered deficient under current medical knowledge. It has been demonstrated that reduction of serum cholesterol levels even to levels higher than those considered normal for the age and sex of the patient being treated result in an increased lifespan for a patient so treated. Reduction of serum cholesterol to normal levels is even more advantageous.

The invention now being generally described, the same will be better understood by reference to the following example which is provided for purposes of illustration only and is not to be considered limiting of the invention unless so specified.

EXAMPLE

Materials and Methods

Adrenal RNA preparation, cell-free translation, immunoprecipitation, and NaDodSO$_4$ gel electrophoresis were done as described (Miller et al., *Endocrinology* (1982) 111:1358–1367). Placental RNA was prepared by guanidine thiocyanate/LiCl extraction (Cathala et al., *DNA* (1983) 2:329–335) and RNA from primary cultures was prepared as described (Voutilainen et al., *J. Clin. Endocrinol. Metab.* (1986) 63:202–207). One 63-mer and three 72-mers corresponding to various regions of the bovine P450scc cDNA sequence (Morohashi et al., *Proc. Natl. Acad. Sci. USA* (1984) 81:4647–4651) were produced using a non-commercial synthesizer (Warner et al., *DNA* (1984) 3:401–411): the sequences and hybridization characteristics of these oligonucleotides were described in a publication by the present inventor (Matteson et al, *Endocrinology* (1986) 118:1296–1305. Dot and Northern blots were done as described in (Voutilainen et al., *J. Clin. Endocrinol. Metab.* (1986) 63:202–207). A 27-mer (see Results) was produced on an Applied Biosystems synthesizer. Oligonucleotides were end-labeled with $\gamma[^{32}P]ATP$ by polynucleotide kinase.

Cloned cDNA was cleaved from λgt10, cloned directly into pUC13 and pUC18 and appropriate fragments were sub-cloned into M13 mp10 and mp11 for dideoxy sequencing (Biggin et al., *Proc. Natl. Acad. Sci. USA.* (1983) 80:3863–3967). Primer extension was done employing 10 µg of human adrenal poly(A)+RNA and 0.1 pmol of the $^{32}$P-labeled 27-mer.

A panel of 15 clonal mouse/human somatic cell hybrid lines was isolated and characterized as described previously (Mohandas et al., *Somat. Cell Mol. Genet.* (1986) 12:89–94). Karyotype analysis was done on each hybrid clone at the time the cells were harvested for DNA extraction; at least 30 G-banded metaphases were photographed and analyzed for each hybrid clone. DNA was isolated (Yen et al., *Somat. Cell Mol. Genet.* (1984) 10:561–571), digested with HindIII and displayed by agarose gel electrophoresis. Gels were blotted and probed with $^{32}$P-labeled P450scc cDNA by Southern transfers (Chung et al., *DNA* (1985) 4:211–219).

Placenta tissue was minced and cultured directly on Falcon plastic dishes in 45% Medium 199, 45% medium F12, 10% fetal bovine serum, 2 mM glutamine, and 50 µg/ml gentamycin in a 5% $CO_2$/95% air atmosphere.

Results

The cell-free translation patterns on polyacrylamide gels of polyadenylated RNA from the adrenal of a patient with Cushing's disease, from an adrenal carcinoma, and from normal tissues are quite similar. Aliquots of these translations were immunoprecipitated with anti-P450scc IgG. Since ACTH stimulates P450scc mRNA accumulation in cultured bovine adrenal cells (John et al., *Proc. Natl. Acad. Sci. USA* (1984) 81:5628–5632), it was expected that RNA from the adrenal of the patient with Cushing's disease would be relatively enriched in P450scc mRNA, as was seen. All four RNAs gave similar patterns the differences in intensities of the immunoprecipitated P450scc band reflects the amount of radioactivity loaded on the gel, not the relative abundance of P450scc mRNA in each RNA sample. The co-precipitating bands of 32,000 and 34,000 daltons seen in the human samples were not seen in the bovine samples run on the same gel or in other experiments (Matteson et al., *Biochem. Biophys. Res. Commun.* (1984) 120:264–270). The nature of these bands is unknown. Based on the fraction of incorporated [$^{35}$S]methionine radioactivity found in the specific P450scc bands, human P450scc mRNA represents less than 0.5% of total human adrenal mRNA.

Identification and Sequence of P450scc cDNA

The construction of a human adrenal cDNA library in λgt10 used in this Example: the synthesis and characteristics of oligonucleotides SCC-1, 2, 3 and 4: and their use to identify the 818 bp human P450scc cDNA fragment λhSCC-36 have been described in the prior publication by the present inventor identified above. A 159 bp EcoRI/Pst fragment from the 5′ end of that cDNA was used to reprobe the amplified cDNA library, identifying 30 putatively positive clones. These were then probed with oligonucleotide SCC-2, a 72-mer corresponding to the sequence encoding amino acids 181–204 of bovine P450scc, identifying two positives. The phage containing the longer insert was designated λhaSCC-71. The λhaSCC-71 cDNA was subcloned, mapped and sequenced. This cDNA contains an open reading frame encoding 464 amino acids of human P450scc: however, by analogy with the bovine sequence, it lacks the codons for the leader peptide and 17 amino-terminal amino acids.

A $^{32}$P-labeled, 27-base oligonucleotide corresponding to the 5' end of the λhaSCC-71 cDNA was prepared and hybridized to one of the same human adrenal polyadenylated RNA samples used in the polyacrylamide gel analysis described above. The 27-mer was used to prime reverse transcription of cDNA and the primer-extended material was analyzed on a denaturing gel, producing a sharp band of about 255 bases (including the 27-base primer). The presence of this single sharp band indicates that virtually all human adrenal P450scc mRNA molecules are about 1850 bases long (excluding the poly A tail) and have the same 5' cap site. Longer P450scc cDNA clones could not be found in the adrenal cDNA library. Therefore, the synthetic 27-mer was used to screen a human testicular cDNA library (K. Fong, Clontech). Several positives were identified and characterized, and the longest, designated λhtSCC-2, was sequenced (FIGURE). Excluding the poly A tail, this clone contains 1821 bases encoding the entire pre-protein, the entire 3' untranslated region and 44 bases of the 5' untranslated region. The corresponding regions of the testicular and adrenal cDNA clones are identical, as expected from the presence of a single P450scc gene in the human genome.

Chromosomal Location of the Human P450scc Gene

Southern blots of human genomic DNA cleaved with five restriction endonucleases and probed either with the bovine-sequence P450scc oligonucleotides or with cDNA clone λhSCC-36 indicate the human genome contains a single P450scc gene. Similar studies indicate the bovine genome also has a single P450scc gene (John et al., Proc. Natl. Acad. Sci. USA (1984) 81:5628-2632). To determine the chromosomal location of this unique human gene, DNA from a panel of 15 mouse/human somatic cell hybrids were examined using λhaSCC-71 cDNA as probe. DNA from 7 of the 15 cell lines contained a 23 kb HindIII fragment hybridizing to P450scc cDNA: correlation of the known human chromosomal components of each cell line with the positively hybridizing cell lines indicates that chromosome 15 carries the P450scc gene, as the pattern of cell lines containing the P450scc gene and chromosome 15 is identical. All other chromosomes show 4 or more cell lines discordant with the P450scc pattern.

Placental Expression of P450scc

Northern blotting of RNA from 10- and 25-week gestation human placentas suggests the relative abundance of P450scc mRNA is greater in early gestation. This placental P450scc mRNA can be regulated by cAMP. The dot blots show that 4 days of primary culture significantly decreased the abundance of P450scc mRNA in 20-week placenta, but that two-days treatment with 1 mM cAMP increased P450scc mRNA back to initial levels.

Significance of Experimental Results

The coding sequence of the human P450scc cDNA is 82% homologous to the bovine sequence, while the amino acid sequences are 72% homologous. With the introduction of only 7 gaps in the 3' untranslated regions, the 214 bases in the human sequence are 69% homologous to the corresponding regions of the 264 base bovine 3' untranslated region. The nucleotide differences between the two species appear to cluster nonrandomly. In the coding sequences, five regions totalling 47 bases (3% of the total) have 40 nucleotide changes (14% of the total): the cluster of differences at amino acids 292-297 contains an additional codon not found in the bovine sequence. By contrast, 5 other regions encompassing 120 amino acids (23% of the total) have only 5 amino acid changes (3.4% of the total) (Table 1). This pattern and degree of homology is different from that seen for other bovine and human proteins such as growth hormone, prolactin and proopiomelanocortin (Miller et al. 1983. In Brain Peptides, Krieger, Brownstein and Martin, eds., John Wiley and Sons, New York, pp 15-78). This conservation suggests these regions are important to enzymatic function.

TABLE 1

Clusters of nucleotide differences and amino acid identities in human and bovine P450scc. Locations refer to the amino acid numbers shown in the Figure.

| Clustered Differences | | Clustered Homologies | |
|---|---|---|---|
| Amino Acid Location | Nucleotide Changes | Amino Acid Location | Amino Acid Changes |
| 21-24 | 7/8 | 50-68 | 9/19 |
| 42-44 | 6/7 | 81-108 | 3/28 |
| 193-195 | 6/7 | 321-344 | 1/24 |
| 292-297 | 13/16 | 374-398 | 0/25 |
| 307-309 | 8/9 | 450-473 | 1/24 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide sequence endoding human P450scc.

2. The sequence of claim 1, wherein said sequence encodes a polypeptide having cholesterol side chain cleavage activity and at least 90% sequence identity with amino acids 1 to 521 of the amino acid sequence set forth in the FIGURE.

3. The sequence of claim 2, wherein substantially all differences between the amino acid sequence of said polypeptide and the amino acid sequence set forth in the FIGURE are located in regions defined by amino acids 21-24, 42-44, 193-195, 292-297, and 307-309.

4. The sequence of claim 2, wherein substantially all amino acids in the regions defined by amino acids 50-68, 81-108, 321-344, 374-398, and 450-473 are identical to the amino acid sequence set forth in the FIGURE.

5. The sequence of claim 1, wherein said polypeptide is identical to the amino acid sequence set forth in the FIGURE.

6. The sequence of claim 1, wherein said sequence has at least 90% sequence identity with nucleotides 1 to 1563 of the nucleotide sequence set forth in the coding region of the FIGURE and encodes a polypeptide having cholesterol side chain cleavage activity.

7. The sequence of claim 4, wherein said sequence is substantially homologous to the polynucleotide sequence set forth in the FIGURE.

8. A functional DNA construct capable of expressing human P450scc comprising (a) a transcription initiation region functional in a unicellular organism, (b) a structural gene according to claim 1 encoding human P450scc, and (c) a transcription termination region.

9. Isolated human genomic DNA consisting essentially of DNA encoding human P450scc.

* * * * *